United States Patent
Eichhorn et al.

(10) Patent No.: US 8,987,669 B2
(45) Date of Patent: Mar. 24, 2015

(54) LASER APPARATUS FOR DETERMINATION OF INK DRYNESS

(71) Applicants: Wade R. Eichhorn, Minneapolis, MN (US); Kristian G. Wyrobek, Minneapolis, MN (US)

(72) Inventors: Wade R. Eichhorn, Minneapolis, MN (US); Kristian G. Wyrobek, Minneapolis, MN (US)

(73) Assignee: 7-Sigma, Inc., Minneapolis, MN (US)

( * ) Notice: Subject to any disclaimer, the term of this patent is extended or adjusted under 35 U.S.C. 154(b) by 180 days.

(21) Appl. No.: 13/788,993

(22) Filed: Mar. 7, 2013

(65) Prior Publication Data

US 2014/0250988 A1     Sep. 11, 2014

(51) Int. Cl.
*G01N 21/55*     (2014.01)
*G01N 21/3554*     (2014.01)
*G01N 21/359*     (2014.01)

(52) U.S. Cl.
CPC .......... *G01N 21/3554* (2013.01); *G01N 21/359* (2013.01)

USPC .................................. 250/339.11; 250/339.1

(58) Field of Classification Search
CPC .. G01N 21/3554; G01N 21/359; G01N 21/55
USPC .............. 250/339.1, 339.11; 347/101; 399/44
See application file for complete search history.

(56) References Cited

U.S. PATENT DOCUMENTS 8,236,164 B2 * 8/2012 Gustafsson et al. .......... 205/788
8,750,732 B2 * 6/2014 Ishii et al. ....................... 399/44

* cited by examiner

*Primary Examiner* — Mark R Gaworecki
(74) *Attorney, Agent, or Firm* — Mark A. Litman & Associates, P.A.

(57) ABSTRACT

An apparatus determines the dryness of inked paper using laser light absorption technique for application in inkjet printers. Direct in-line feedback is provided as to the effectiveness of the drying of the ink placed deposited upon paper or other media. Associated laser system designs and the technologies employed in the determination of drying efficiency of inks and other liquids placed upon a media are enabled.

18 Claims, 8 Drawing Sheets

Water Absorption Spectrum

*Fig. 1* Water Absorption Spectrum

Fig. 2 Absorption Spectrum, 900-2000nm, of black and magenta water based ink.

*Fig. 3* FTIR spectral analysis of water placed on paper and black paper

Fig. 4 FTIR spectral analysis of ink placed on paper and paper dried

Fig. 5 TGA of dried paper sample

Fig. 6 TGA of Magenta ink

Fig. 7     Table of ink water and glycol percentage contents

| INK | % Water | % Glycol |
|---|---|---|
| Magenta | 55.7 | 24.9 |
| Cyan | 58.1 | 24.9 |
| Yellow | 63.5 | 22.8 |
| Black | 74.4 | 8.5 |

Fig. 8A Laser optical system of invention

Curretsy Alkea Laser Company

Fig. 8B Laser optical system of invention utilizing multiple wavelengths of light.

LASER APPARATUS FOR DETERMINATION OF INK DRYNESS

BACKGROUND OF THE ART

1. Field of the Invention

This invention relates to an apparatus for determining the dryness of inked paper using laser light absorption technique for application in inkjet printers. The invention provides direct in-line feedback as to the effectiveness of the drying of the ink placed deposited upon paper or other media. This disclosure describes the associated laser system designs and the technologies employed in the determination of drying efficiency of inks and other liquids placed upon a media.

2. Background of the Art

High speed production inkjet printers print at speeds exceeding 300 pages per minute are cost efficient color printers for many high volume printing applications. Water based inks employed provide lower cost and are more environmentally friendly than other inks. However, the water-based ink may not dry fast enough before the paper is folded or printed on the reverse side, causing print or image quality. The drying of water based inks currently use near infrared (NIR) heating elements, comprised of heating lamps, which can dry water/glycol based inks by heating to vaporize the water and glycol components of the ink formulation. The drying of water-based inkjet ink applied to media by high speed continuous forms inkjet printers is an evolving post-processing product for the printing market. Currently no known method is employed to determine the efficiency of the drying system in real time within the inkjet printer. A method by which real time feedback of the performance of the printer drying system to the controller would be beneficial to the desired dryness of the inked media.

High speed production inkjet printers manufactured by Ricoh, Canon, Kodak, Xerox and others, use aqueous based inks in many of their products. Water is the largest component, by weight comprising as much as 60%. Other liquid components include glycol and other semi-volatiles. These liquid components spread out onto, and are absorbed into, the print media. The spreading function and absorption into the media is dependent upon the media composition. For example, plain uncoated paper, is absorbs the liquid more readily than a coated paper. Oko, Asaf, et. al (2010) "Imbibition of picoliter water droplets on coated inkjet papers", NIP26 and Digital Fabrication 2010 Technical Proceedings, pp 475-478. describe the wetting of ink on plain and coated papers with spreading observed over 1 ms of time. K. Vikman, et. al. (2005) "Water Fastness of Ink Jet Prints on Modified Conventional Coatings, IS&T Volume 20, N0.2, April 2005, describe the analysis of various coated papers absorption of ink utilizing FTIR and Raman Spectrometry methods. T. Hartus, (1999), "Thermal Analysis of Ink-Substrate Interactions and Drying in Ink Jet Printing" Graphic Arts in Finland, 28 (1999)1, 3-10 describes TGA and DSC methods to evaluate papers with differing pulp content and the resultant absorption of inks into the papers and the evaporation energies of various inks. Eichhorn et. al, (2013), "Determination of Dryness of Water-based Inket Ink", NIP29 Digital Printing Conference, September 2013, (proceedings yet to be published at time of patent application), describe FTIR and TGA analysis of wet and dried inked paper as a function of dryness determination after the inked paper had been exposed to a drying system.

Evaporation of the water and glycol at room temperature is too slow for high speed print applications, where the paper is either stacked or rolled up immediately after printing. Therefore drying of the paper within seconds of depositing the ink to the printed page is advantageous. For water based inks, current drying methods use Near Infrared (NIR) lamps that are positioned along the direction of movement of the printable substrate after the inkjet printing heads, to rapidly heat up the ink and media substrate to vaporize the water and glycol. The NIR lamps have light emission spectra at wavelengths from about 800 to 1100 nm (by way of non-limiting examples). One NIR system is manufactured by Adphos USA (Brookfield, Wis.) that employs multiple NIR heating units consisting of NIR lamps with "focusing" shields above and below the paper in the printer. While massive heat can be generated by NIR lamps, the absorption efficiency into water is very low in the NIR region and much heat is needed to effectively dry the ink sufficiently to avoid smearing or blocking (adherence between sheets caused by binding through the inks). The determination of the dryness of the heated surface is important to the efficiency of the drying system and assurance that smearing and blocking do not occur. An in-line immediate feedback system determining the moisture content within the inked media would be a beneficial component of the printer drying system, which this invention addresses.

High speed production inkjet printing is an expanding market technology. The drying of water-based inkjet ink applied to media by high speed continuous forms inkjet printers, is an evolving post-processing product for the printing market. The efficiency of the dryers to remove the water and glycols, and other semi-volatile components of the ink can be determined by laboratory analytical techniques. Analytical methods employed to determine the level of dryness of inkjet printed paper utilizing Thermal Gravimetric Analysis (TGA), Fourier Transform Infrared Spectrometry (FTIR) may yield baseline characterizations by which the invention described within is characterized against. Experimental testing FTIR and TGA methods are described here within, showing the ability to discern the level of dryness of a water-based inkjet printed paper sample. The methods provide effective tools for analysis of drying, and point to methods by which real time in-line printer feedback may be developed and characterized as those employed in the invention.

SUMMARY OF THE INVENTION

Figure 1:
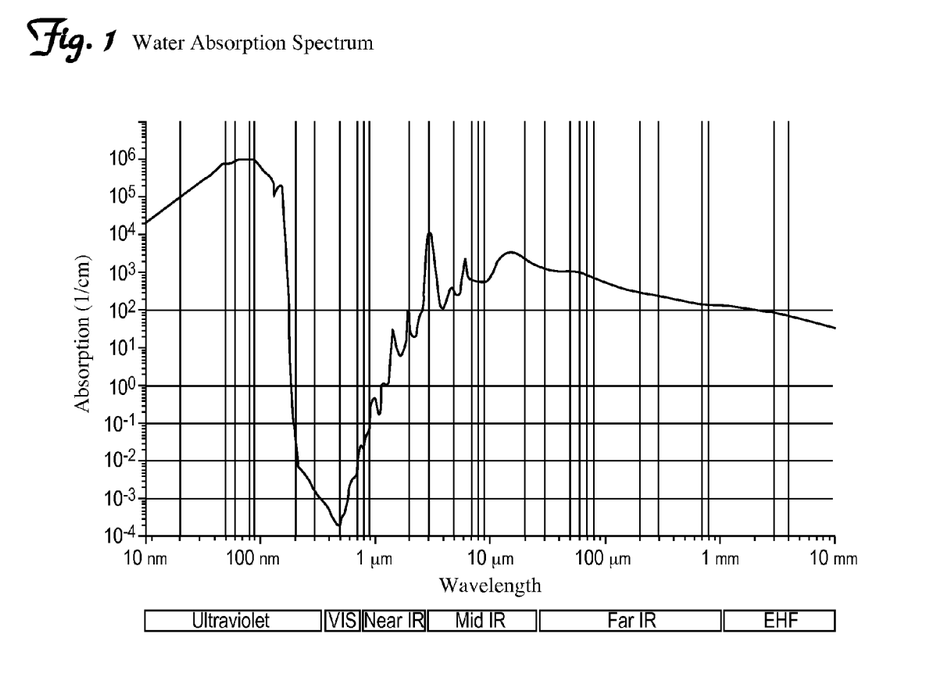
FIG. 1 is a Water Absorption Spectrum

The efficiency and positional degree of performance of the dryers to remove water and glycols, and other semi-volatile components of the ink can be determined by optical analytical techniques. Spectral analysis using UV-VIS-NIR and FTIR are well understood analytic tools for chemical identification and material characterization. These techniques have been determined in the present invention to be applicable to the determination of dryness of inked paper by observing the optical absorption level of water within the paper. Light transmitted through paper or reflected from the surface of paper, provides information on the amount of moisture within by the amount of absorption of the light. Water absorbs light efficiently in the UV and the IR spectral regions and can be determined by optical means. FIG. 1 is an absorption spectrum of water showing those peak regions of absorption. The region at about 2900 nm wavelength, the absorption peak is of interest because that is the spectral region where a laser diode optical system may be applied for real time, in-line, analysis of water content, providing immediate feedback to the drying system controller.

The invention includes a system for determining dryness of an inked absorbent substrate, the system comprising: a laser diode emitting at a predetermined wavelength, an electromagnetic sensor responsive to the predetermined wavelength, the electromagnetic sensor being in information communication with a processor, the processor configured to receive data originated in the sensor to identify moisture content in ink applied to the absorbent substrate.

An example of a method for practicing technology within the generic scope of the present technology includes a method of sensing dryness of a printed absorbent surface comprising printing the absorbent surface with an ink comprising water or a semivolatile ink, drying the ink, after drying the ink, exposing inked and dried surface of the absorbent substrate to electromagnetic radiation having a wavelength between 1000 nm and 4000 nm, a sensor capturing electromagnetic radiation transmitted through or reflected from the inked and dried absorbent surface, the sensor transmitting data responsive to captured electromagnetic radiation to a processor, the processor receiving the transmitted data and executing code to determine remaining water or semivolatile content in ink at inked, dried and exposed areas.

DETAILED DESCRIPTION OF THE INVENTION

The efficiency of dryers to remove water and glycols, and any semi-volatile components of the ink can be determined by optical analytical techniques. Spectral analysis using UV-VIS-NIR and FTIR are well understood analytic tools for chemical identification and material characterization. These techniques can be applied to the determination of dryness of inked paper by observing the optical absorption level of water within the paper. Light transmitted through paper or reflected from the surface of paper, provides information on the amount of moisture within by the amount of absorption of the light. Water absorbs light efficiently in the UV and the IR spectral regions and can be determined by optical means. FIG. 1 is an absorption spectrum of water showing those peak regions of absorption. At 2900 nm wavelength, the absorption peak is interest because that is the spectral region where a laser diode optical system may be applied for real time, in-line, analysis of water content, providing immediate feedback to the drying system controller.

The invention includes a system for determining dryness of an inked absorbent substrate, the system comprising: a laser diode emitting at a predetermined wavelength, an electromagnetic sensor responsive to the predetermined wavelength, the electromagnetic sensor being in information communication with a processor, the processor configured to receive data originated in the sensor to identify moisture content in ink applied to the absorbent substrate.

The system may have the laser diode emit at a wavelength between 1000 and 3000 nm, such as at a wavelength within ±20 nm of 1450 nm, 1550 nm, and 1950 nm along with 2900 nm. The processor may have a stored lookup table that is used by execution of code by the processor to compare the data received with the lookup table to determine dryness of ink with respect to water and/or semivolatile liquid within the previously applied to the absorbent surface.

The sensors may receive reflected electromagnetic radiation or transmitted electromagnetic radiation to originate the data from the sensor.

The processor may have a stored lookup table that is used by execution of code by the processor to compare the data received with the lookup table to determine dryness with respect to organic semivolatile carrier content of ink previously applied to the absorbent surface. The organic semivolatile may contain a glycol.

A method for practicing the present technology may include a method of sensing dryness of a printed absorbent surface comprising printing the absorbent surface with an ink comprising water or a semivolatile ink, drying the ink, after drying the ink, exposing inked and dried surface of the absorbent substrate to electromagnetic radiation having a wavelength between 1000 nm and 4000 nm, a sensor capturing electromagnetic radiation transmitted through or reflected from the inked and dried absorbent surface, the sensor transmitting data responsive to captured electromagnetic radiation to a processor, the processor receiving the transmitted data and executing code to determine remaining water or semivolatile content in ink at inked, dried and exposed areas.

The method may use electromagnetic radiation having a wavelength between 1000 nm and 4000 nm is emitted from a laser diode, such as wherein the laser diode emits at a wavelength within ±20 nm of 1450 nm, 1550 nm, and 1950 nm along with 2900 nm. The method may have the processor execute code to compare received data to a lookup table stored in memory of the processor to determine remaining water or semivolatile content in ink at inked, dried and exposed areas. The method may have the processor execute code to compare received data to a lookup table stored in memory of the processor to determine remaining water content in ink at inked, dried and exposed areas.

Experimental Background

FTIR, TGA and GCMS analytical techniques here have been applied to the determination of dryness of water-based inkjet ink on paper. Samples of paper with water-based ink were tested after printing and after drying. Paper without print was tested as a control for each test. Water and glycol are the major semi-volitile components within ink formulations and are foremost in the consideration of dryness of inked paper after drying. Water has strong spectral absorption peaks in the UV and in the IR wavelengths. FTIR Spectrometry shows clearly the water absorption peak in the IR at about 2900 nm wavelength and therefore is one of the methods herein chosen in the determination of dryness according to the present invention. TGA records the weight loss as the material is heated. TGA can determine the percent of water and other ink components that are driven off the material under test as heat is applied. GC-MS used with micro-extraction head space testing can determine the amount of volitiles evolved as the inked paper is heated. Each of these analytical methods are applied to paper, paper with water-based ink applied, and to inked paper that has been dried.

Figure 3:
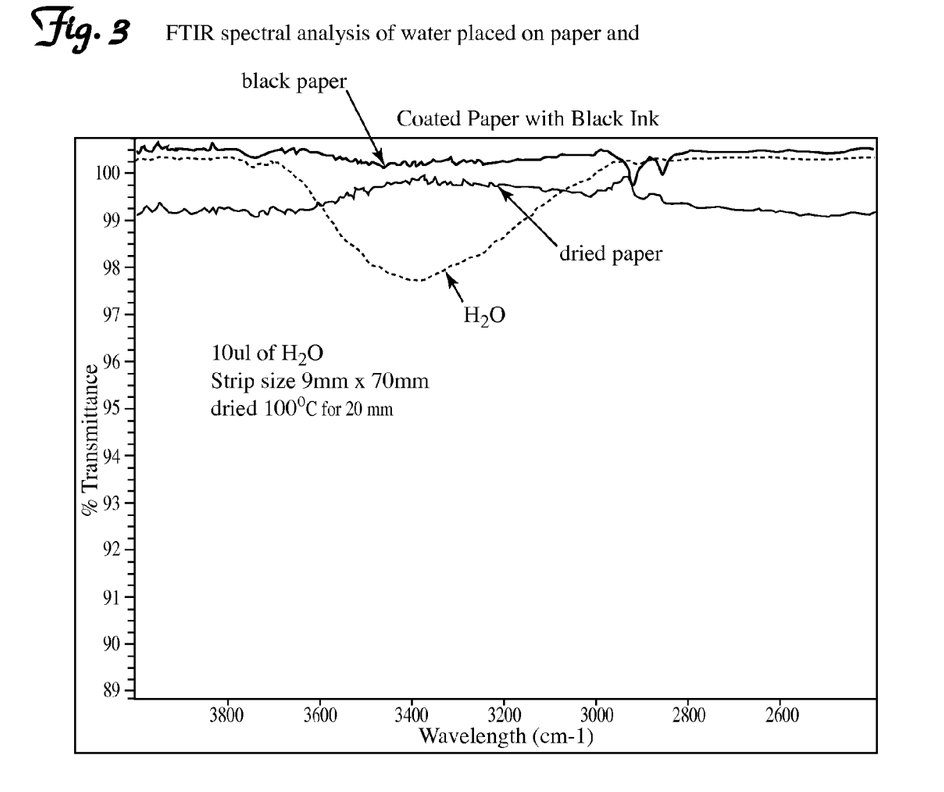
FIG. 3 is an FTIR spectral analysis of water placed on paper and paper dried
Figure 4:
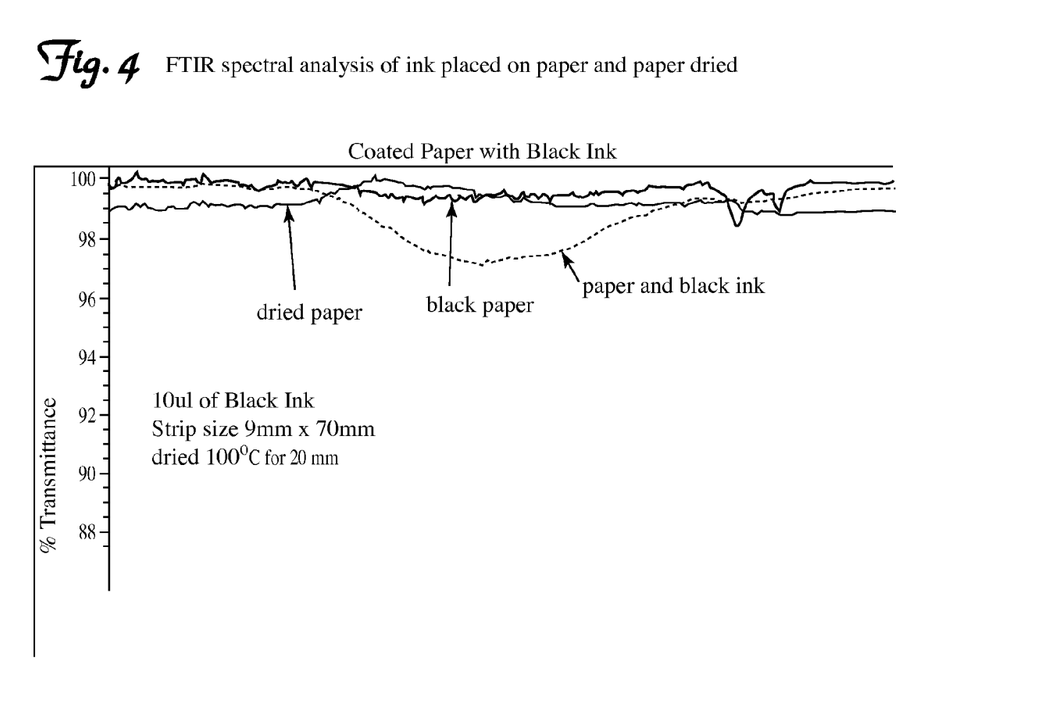
FIG. 4 is an FTIR spectral analysis of ink placed on paper and paper dried

First order analysis of dryness can simply be seen by comparison of before and after drying of the paper with FTIR and TGA. Since water is the major component to be dried from the paper, an initial analysis was conducted by spreading 10 micro liters of water onto a 9 mm wide by 70 mm long (16 nano liters/mm² H₂O) piece of commercial inkjet paper that has a surface coating suitable for inkjet printing. FIGS. 3 and 4 are data showing blank paper, water on paper, and dried paper. The paper was placed into the FTIR ATR fixturing. The FTIR spectra, FIG. 3 shows water's absorption peak is at 2900 nm, or 3500 wave numbers and indicates that the blank paper contained some moisture as seen with a slight dip in the percent transmission. The water content after applying 10 micro liters of water, is clearly seen by the dip of percent transmission to 97.5%. The removal of the water after drying at 100° C. for 20 minutes, is seen by the "convex" percent transmison at 2900 nm. The TGA data, FIG. 4, of the same blank paper and watered paper, shows the percentage weight (% wt) loss of the water component as the paper is heated through 250° C.

Micro-extraction head space analysis using GC-MS is applied to the determination of dryness to determine the amount of volatiles that are vaporized from the heating of an inked piece of paper. In this technique, a small piece of measured dimensions and weight are placed into a small head space chamber (glass vile) and heated to 200° C. The vapors that are driven from the paper are absorbed on a micro fiber over a period of time. The micro fiber absorbs the semi-volitiles such as glycols. The fiber is then desorbed into the GC-MS. Analysis of the resultant specta identifies the chemicals which have been collected and the amount of the material. This technique, though not applicable to water vapor, will enable the qualitative and quantificative analysis of the volotile chemical emitted, and is relateable back to the TGA and FTIR data.

Ink testing was first analyzed by the present technology using TGA to determine the temperatures at which the comprising components are evaporated. Each color of ink has different volume, by percent mass, of water and glycol components and can be determined by TGA. Each of the inks were heated through 800° C. to determine the evaporation temperatures and percentage by weight of all the ink components, including pigments. In addition, mixtures of known ink components were mixed in different ratios and TGA performed on those mixtures to help further characterize the data on each ink. These two TGA tests were conducted to provide baseline information on the inks to be studied. In addition, Infrared spectrometry, FTIR, was performed on each of the inks to help further identify components of the inks. Furthermore, UV-VIS spectral analysis and Differential Scanning Calorimetry (DSC) were used to further identify optical and thermal properties, including heat flow, of the inks. This is not relevent to the drying analysis of the ink, but provides additional information to better understand the inks to be used in optimizing the practices of the present invention.

Commercially available ink used in a very high speed production inkjet printer was analyzed by TGA, FTIR and GC-MS. As described in the proceeding section, each of the color inks were analyzed for the percent of water and glycol components. Each ink was then applied to a coated inkjet paper, 9 mm×70 mm dimensions, in the amount of 10 microliters across the surface. The inked papers were analyzed before and after drying for the change in moisture content of a known amount of ink deposited upon a measured area.

Figure 6:
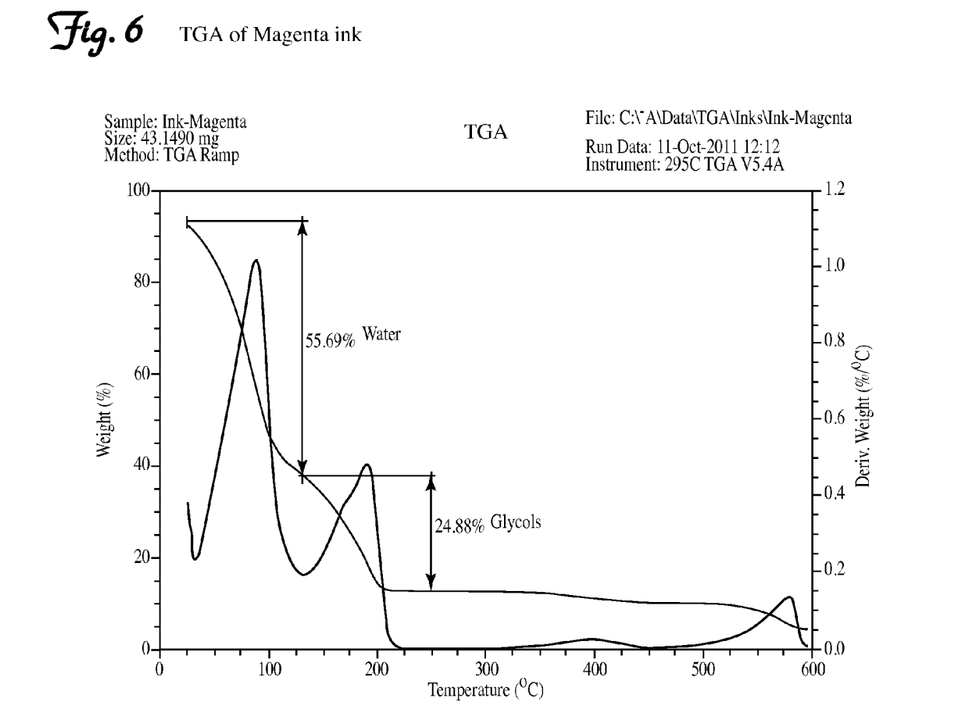
FIG. 6 is a TGA of Magenta ink
Figure 7:
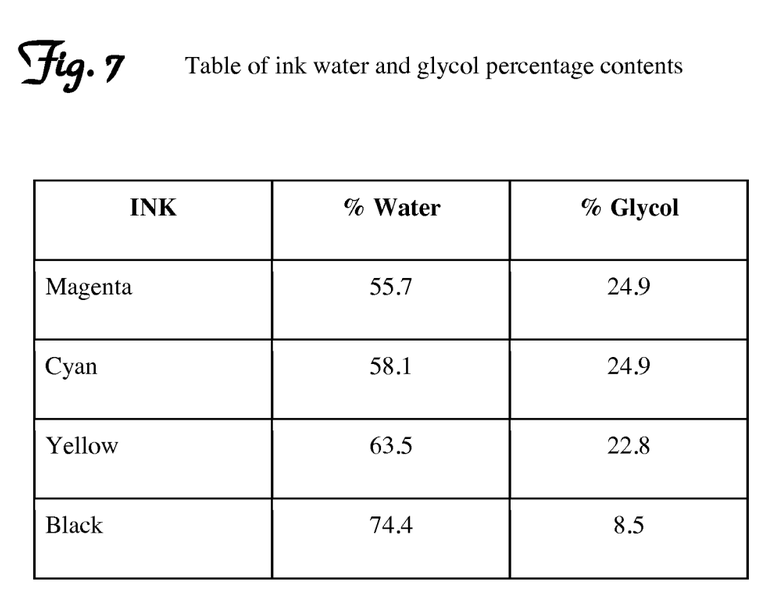
FIG. 7 is a Table of ink water and glycol percentage contents

FIG. 6 is a TGA analysis of the magenta ink, showing the relative percent by weight of the water and glycol components. FIG. 7 (Table 1) is a summary of the primary color inks and the weight ratios of water and glycol obtained by TGA. Knowing the starting ratio, will help determine the relationship to dryness to be determined in this study.

Figure 5:
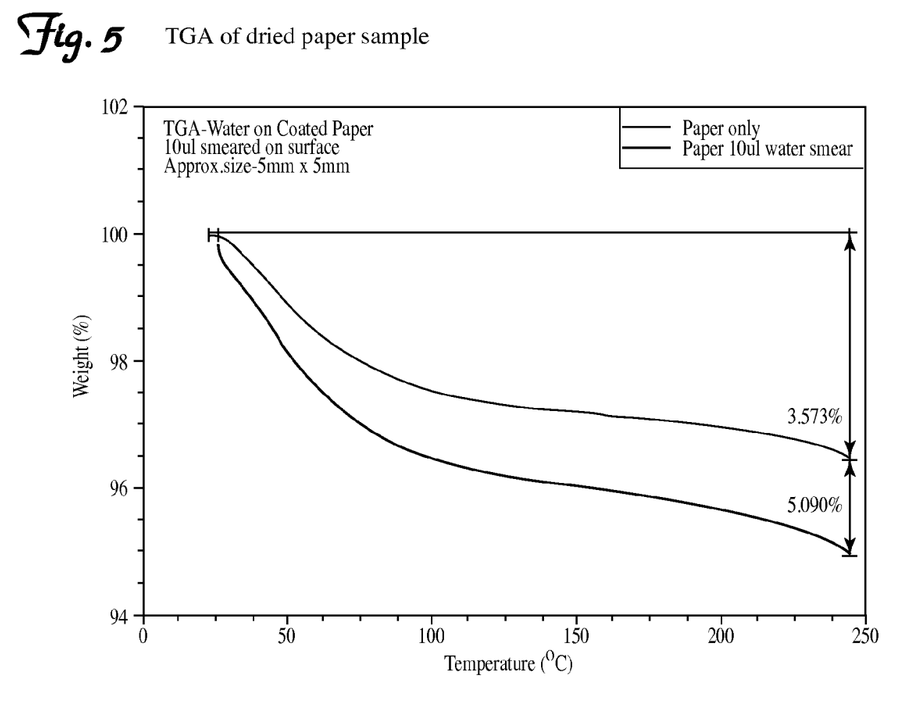
FIG. 5 is a TGA of dried paper sample

The first ink analyzed was the black ink. As given in FIG. 7 (Table 1), the water content was found to be 74% and the glycol 8% by wt. After applying 10 microliters of the ink to the 630 mm² strip of paper (16 nl/mm²), the strip was then placed into the FTIR-ATR fixturing and tested. A 25 mm² piece of the paper was then tested with the TGA to a temperature of 250° C. The inked paper was then dried at 100° C. for 20 minutes and re-tested in the FTIR and TGA. FIG. 5 is the resultant FTIR spectraa and FIG. 6 is the TGA plot. Each clearly show the significant reduction in water after drying of the inked paper.

The laboratory techniques described serve as a basis by which to characterize and quantify the efficiency of laser optical systems according to various embodiments of the invention. The choice of specific lasers that emit light at the absorption peaks of water, provide a simplified, concentrated system as compared to that of an FTIR optical arrangement. The invention employs laser diodes specific to the spectral absorption peaks of water, in an optical system that interrogates transmitted and/or reflected light from an inked media for the percentage of light absorption at the spectral absorption peaks of water. As with the examples of FTIR analysis described in this section, the laser optical system of the invention provide a method by which the level of dryness can be determined. The invention will provide immediate feedback to the dryer controller through micro processor control of the intensity readings of the laser optical system.

FIG. 1 the Absorption Spectrum for water. Water has major absorption peaks in the ultravilot region of the spectrum and then again in the infrared region with largest absorption after or about 2900 nm or 3500 wave number. The region from 400 to 1000 nm electromagnetic radiation is transmitted through water and not until 1100 nm does it begin to be absorbed more effeciently. Peaks in the 1450, 1550 and 1950 nm regions provide sufficient absorption energy to be considered for laser drying determination. The 2900 nm peak is of special interest because of the maximum absorption efficiency available and diode lasers of sufficient power are available that emit at that wavelength to be applied to determination of dryness.

Figure 2:
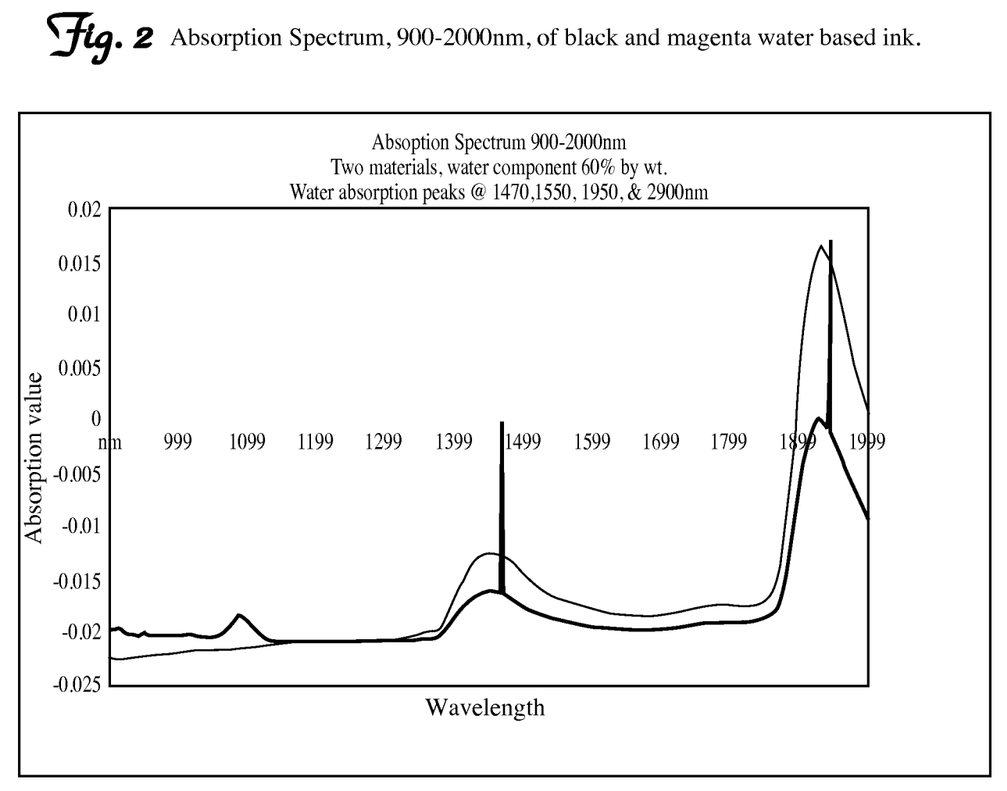
FIG. 2 is an Absorption Spectrum, 900-2000 nm, of black and magenta water based ink

FIG. 2 is the Absorption Spectrum, at 900-2000 nm, of black and magenta water based ink. The two absorption peaks observed for these two inks at 1450 and 1950 are of interest to apply laser diodes with light emission at those wavelength for drying analysis.

FIG. 3 is an FTIR spectral analysis of water placed on paper and the paper dried. Ten micro liters of water was applied to a 9×70 mm piece of coated inkjet paper. The paper spectra were determined by FTIR with the reflective ATR attachment. The resultant reflective spectra clearly show the water absorption peak at 3500 wave numbers, 2900 nm. The paper was then dried at 100° C. This figure clearly shows the ability to discern the dryness of the paper by observing the absorption spectra of water at 2900 nm.

FIG. 4 is an FTIR spectral analysis of ink placed on paper and paper dried. The same experiment was applied as described for FIG. 3. Again, the resultant spectrum of the dried paper compared to the inked paper shows that observing the absorption spectra of water at 2900 nm is an effective step in a method to determine dryness.

FIG. 5 is a TGA plot of the paper sample described in FIG. 3. A small piece of the sample, 5 mm diameter, of the same watered paper of FIG. 3, was analyzed before and after drying. The TGA further verifies the efficiency of drying and is an analytical method to help quantify the percentage of moisture content and resultant drying as seen with the FTIR analysis.

FIG. 6 is a TGA plot of Magenta ink, as an example, determining the ratio of water and glycol components of the ink.

FIG. 7 is a Table of ink water and glycol percentage contents and is of reference in determining the amount of water and glycol contained within an inked sample being dried.

Figure 8A:
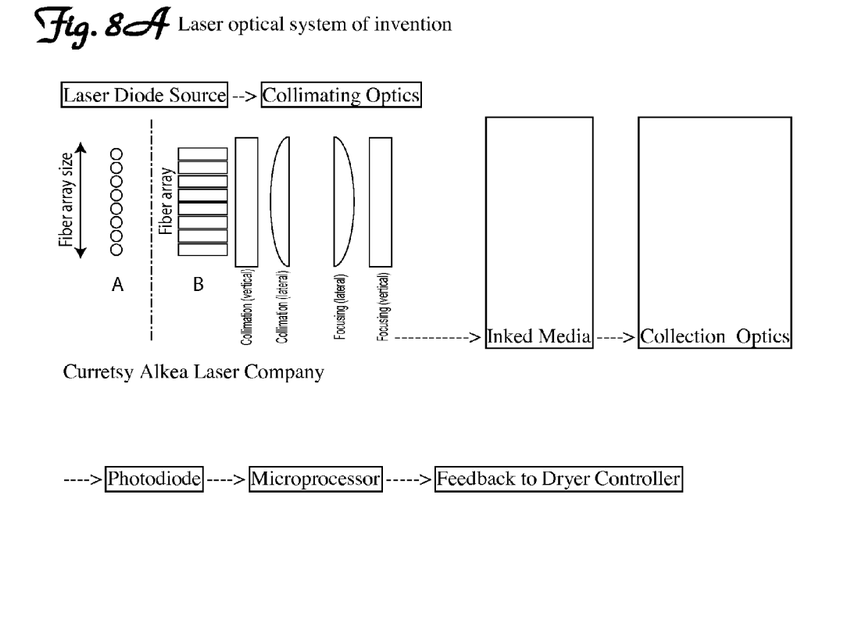
FIG. 8a is a Laser optical system of invention

FIG. 8a depicts a sample laser diode optical system of invention. The diode laser is chosen from IR lasers whose center wavelengths are in the peak regions of water absorption, for example 2900 nm. The laser light is used to sample a region of the inked paper by either transmission or reflection or transmission and reflected light and record the absorption percentage of the light. The optical system may utilize lenses and or fiber optics to shape and focus the beam as well as collect the light and guide it to a photo detection system to analyze the absorption efficiency.

Figure 8B:
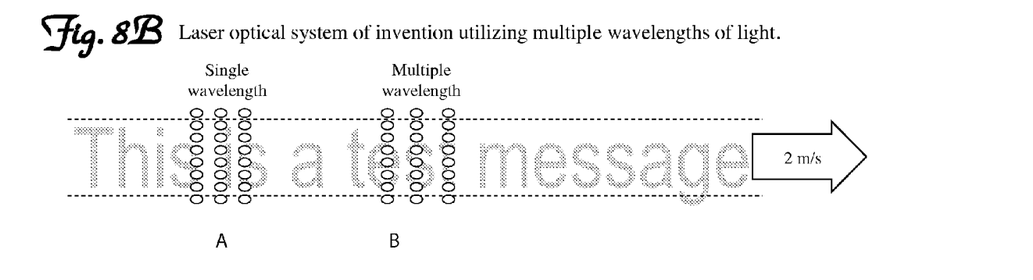
FIG. 8b is a Laser optical system of invention utilizing multiple wavelengths of light

FIG. 8b is a Laser optical system of the invention depicting multiple wavelengths of light with emissions at 1450, 1950 and 2900 nm within the optical system that is depicted in FIG. 8a.

FTIR spectral analysis is an effective tool to determine the presence of water on a surface, within a surface or within a substance. FTIR-Transmission and FTIR-ATR reflectance studies have shown that water absorption at 2900 nm wavelength can be interpeted as to the amount of water that is contained within the material tested. Correlation studies using TGA can confirm and correlate the percentage of water content within the media. thus showing that optical analysis is a viable method of water content determination. Laser diode optical systems are used in LIDAR systems which detect moisture in the field of view in the atmosphere. A similar arrangement may be applied to determination of moisture content within a printed media such as paper that has had ink deposited on it. A transmission or a reflectance laser optical system can be designed to observe the water content within an ink printed media, such as paper, by measuring the level of absorption of incedent laser light. Choosing the wavelength of light to have maximum intensity at one or more major absorption peaks of water allows the absorption ratio to be easily observed. Laser diodes emitting in the IR spectrum, specifically in the 1450, 1550, 1950 and 2900 nm regions, are where the greatest absorption of light by water occurs. A laser diode optical system emitting one or more of those wavelengths would provide the ability to rapidly determine the water content of the inked paper and therefore the amount of dryness of the inked paper. The transmissive and/or the reflective laser light is collected with optics that deliver the analytical photons to a photodetection system. The photodetection system consists of photodiodes whose resultant output waveforms show the variations in light intensities due to the amount of light absorption of moisture, water & glycols, contained withing the sample region being observed by the optical system. A photodetection system may utilize a single laser diode emitting in the 2900 nm region, the largest absorption peak of water. The photodetection system may also utilize multiple wavelengths emissions at additonal water absorption peak regions of 1450 nm, 1550 nm, and 1950 nm along with 2900 nm, and the comparison of the absorption percentage of each. The analysis of the intensity of the collected photons by the photodiodes can be quickly determined by a microprocessing system (by configuration of the processing system to execute software) designed to interpert the resultant intensities as to the amount of moisture content contained within the sampling area. By use of look up tables and other software incorporated within the processing component of the invention, instructions are relayed back to the processor control unit of the drying system of the inkjet printer.

The optical system and method described within this disclosure may use one or more of the laser diodes emitting in the water absorption peak regions of 1450, 1950 and 2900 nano meters wavelengths. The laser diode system embodied in the invention is composed of laser diodes, optical system delivering laser light to the region to be interigated, optical system delivering transmitted or reflected light from the interigated region to a photodiode system and a micro controller system to record and interpert the light intensities of the interigated region as to the percentage of moisture contained within the interigated region. The resultant determination is feed back to the microprocessor controller of the drying system of the printer for adjustments of heating to achieve the desired level of dryness of the inked media. For example, where the drying of the ink was performed with laser radiation and after determining a level of remaining water or semivolatile content in ink at inked, dried and exposed areas, the processor or an operator may alter characteristics of the laser radiation used to dry the ink by at least one parameter selected from the group consisting of laser intensity, laser duration, laser spot size and laser spot overlap. The duration can be enabled by adjusting the speed of the substrate pass-through, but this is less preferred as the efficiency of the process may be altered adversely.

Although specific components, wavelengths, times and temperatures are reported, these are specific examples within the generic scope of the present technology and are not to be read as limiting the generic scope of the invention. The present technology may also be used in the coating of adhesives to surfaces (especially water-based adhesives), decorative coatings to surfaces, and the application of active ingredients to surfaces in high speed printing processes.

The invention claimed is:

1. A system for determining dryness of an inked absorbent substrate, the system comprising: an infrared emitting device emitting at a predetermined wavelength within a range of 1000 nm to 4000 nm, an electromagnetic sensor responsive to the predetermined wavelength, the electromagnetic sensor being in information communication with a processor, the processor configured to receive data originated in the sensor to identify moisture content in ink applied to the absorbent substrate wherein the processor has a stored lookup table that is used by execution of code by the processor to compare the data received with the lookup table to determine dryness with respect to water content on the absorbent surface.

2. The system of claim 1 wherein the infrared emitting device comprises a laser diode emits at a wavelength between 1000 and 3000 nm.

3. The system of claim 1 wherein the infrared laser device comprises a laser diode that emits at a wavelength within ±20 nm of 1450 nm, within ±20 nm of 1550 nm, or within ±20 nm of 1950 nm, along with a laser diode emitting within ±20 nm of 2900 nm.

4. The system of claim 3 wherein the sensors receive reflected electromagnetic radiation or transmitted electromagnetic radiation to originate the data from the sensor.

5. The system of claim 3 wherein the processor has a stored lookup table that is used by execution of code by the processor to compare the data received with the lookup table to determine dryness with respect to organic semivolatile carrier content of ink previously applied to the absorbent surface.

6. The system of claim 5 wherein the organic semivolatile comprises a glycol.

7. The system of claim 1 wherein the sensors receive reflected electromagnetic radiation or transmitted electromagnetic radiation to provide data to the sensor.

8. A system for determining dryness of an inked absorbent substrate, the system comprising: an infrared emitting device emitting at a predetermined wavelength, an electromagnetic sensor responsive to the predetermined wavelength, the electromagnetic sensor being in information communication with a processor, the processor configured to receive data originated in the sensor to identify moisture content in ink applied to the absorbent substrate, wherein the processor has a stored lookup table that is used by execution of code by the processor to compare the data received with the lookup table to determine dryness of ink previously applied to the absorbent surface.

9. The system of claim 8 wherein the sensors receive reflected electromagnetic radiation or transmitted electromagnetic radiation to provide data to the sensor.

10. A system for determining dryness of an inked absorbent substrate, the system comprising: an infrared emitting device emitting at a predetermined wavelength, an electromagnetic sensor responsive to the predetermined wavelength, the electromagnetic sensor being in information communication with a processor, the processor configured to receive data originated in the sensor to identify moisture content in ink applied to the absorbent substrate, wherein at least one the laser emitting device emits at a wavelength selected from the group consisting of within ±20 nm of 1450 nm, within ±20 nm of 1550 nm, and within ±20 nm of 1950 nm, in addition to a laser emitting device emitting at a wavelength within ±20 nm of 2900 nm,
wherein the processor has a stored lookup table that is used by execution of code by the processor to compare the data received with the lookup table to determine dryness with respect to water content of ink previously applied to the absorbent surface.

11. The system of claim 10 wherein the sensors receive reflected electromagnetic radiation or transmitted electromagnetic radiation to provide data to the sensor.

12. A method of sensing dryness of a printed absorbent surface comprising printing the absorbent surface with an ink comprising water or a semivolatile ink, drying the ink, after drying the ink, exposing inked and dried surface of the absorbent substrate to electromagnetic radiation having a wavelength between 1000 nm and 4000 nm, a sensor capturing electromagnetic radiation transmitted through or reflected from the inked and dried absorbent surface, the sensor transmitting data responsive to captured electromagnetic radiation to a processor, the processor receiving the transmitted data and executing code to determine remaining water or semivolatile content in ink at inked, dried and exposed areas.

13. The method of claim 12 wherein the electromagnetic radiation having a wavelength between 1000 nm and 4000 nm is emitted from a laser diode.

14. The method of claim 13 wherein the laser diode emits at a wavelength within ±20 nm of 1450 nm, within ±20 nm of 1550 nm, and within ±20 nm of 1950 nm along with within ±20 nm of 2900 nm.

15. The method of claim 14 wherein the drying of the ink is performed with laser radiation and after determining a level of remaining water or semivolatile content in ink at inked, dried and exposed areas, altering characteristics of the laser radiation used to dry the ink by at least one parameter selected from the group consisting of laser intensity, laser duration, laser spot size and laser spot overlap.

16. The method of claim 13 wherein the processor executes code to compare received data to a lookup table stored in memory of the processor to determine remaining water content in ink at inked, dried and exposed areas.

17. The method of claim 13 wherein the drying of the ink is performed with laser radiation and after determining a level of remaining water or semivolatile content in ink at inked, dried and exposed areas, altering characteristics of the laser radiation used to dry the ink by at least one parameter selected from the group consisting of laser intensity, laser duration, laser spot size and laser spot overlap.

18. The method of claim 12 wherein the processor executes code to compare received data to a lookup table stored in memory of the processor to determine remaining water or semivolatile content in ink at inked, dried and exposed areas.

* * * * *